| (12) United States Patent | (10) Patent No.: US 8,359,085 B2 |
| Hörndler et al. | (45) Date of Patent: Jan. 22, 2013 |

(54) METHOD AND SYSTEM FOR PERFORMING COORDINATE TRANSFORMATION FOR NAVIGATION-GUIDED PROCEDURES UTILIZING AN IMAGING TOOL AND A POSITION-DETERMINING SYSTEM

(75) Inventors: Klaus Hörndler, Nürnberg (DE); Christof Fleischmann, Möhrendorf (DE)

(73) Assignee: Ziehm Imaging GmbH, Nuremberg (DE)

( * ) Notice: Subject to any disclaimer, the term of this patent is extended or adjusted under 35 U.S.C. 154(b) by 577 days.

(21) Appl. No.: 11/670,934

(22) Filed: Feb. 2, 2007

(65) Prior Publication Data

US 2007/0232897 A1 Oct. 4, 2007

(30) Foreign Application Priority Data

Feb. 2, 2006 (DE) .................. 10 2006 004 793

(51) Int. Cl.
*A61B 5/05* (2006.01)

(52) U.S. Cl. ........ 600/424; 600/426; 600/427; 600/429; 378/205

(58) Field of Classification Search .................. 600/424, 600/426, 427, 429; 378/205
See application file for complete search history.

(56) References Cited

U.S. PATENT DOCUMENTS

| 5,769,861 | A | 6/1998 | Vilsmeier |
| 6,527,443 | B1 | 3/2003 | Vilsmeier et al. |
| 6,671,538 | B1 * | 12/2003 | Ehnholm et al. ............. 600/425 |
| 6,932,506 | B2 | 8/2005 | Mitschke et al. |
| 7,010,095 | B2 | 3/2006 | Mitschke et al. |
| 2003/0209096 | A1 | 11/2003 | Pandey et al. |
| 2004/0013240 | A1 * | 1/2004 | Mitschke et al. ............. 378/205 |
| 2005/0163279 | A1 | 7/2005 | Mitschke et al. |
| 2007/0106282 | A1 | 5/2007 | Lavallee |

FOREIGN PATENT DOCUMENTS

| DE | 199 17 867 | 11/2000 |
| DE | 101 37 914 | 5/2002 |
| DE | 102 02 091 | 8/2003 |
| DE | 103 60 025 | 7/2005 |
| EP | 1 579 803 | 9/2005 |
| FR | 2 854 318 | 11/2004 |
| WO | WO 2005/032390 | 4/2005 |

OTHER PUBLICATIONS

European Search Report, dated May 22, 2007, EP 1815814, 5 pg.

* cited by examiner

*Primary Examiner* — Brian Casler
*Assistant Examiner* — Joseph M Santos
(74) *Attorney, Agent, or Firm* — Knobbe Martens Olson & Bear LLP

(57) ABSTRACT

The invention relates to a method and device for performing coordinate transformation for navigation-guided procedures using an imaging diagnostic tool, especially an X-ray diagnostic tool, and a position-determining system. In the vicinity of the image receiver, the diagnostic tool has one or more three-dimensional reference structure that can be touched with a pointer of a position-determining system. From the known geometry of the three-dimensional reference structure and the coordinates of the touched points determined by the position-determining system, a coordinate transformation is created between the coordinate system of the diagnostic tool and the coordinate system of the position-determining system. Navigation for an instrument captured by the position-determining system can be performed in reconstructed images of the diagnostic tool after the registration procedure.

17 Claims, 3 Drawing Sheets

METHOD AND SYSTEM FOR PERFORMING COORDINATE TRANSFORMATION FOR NAVIGATION-GUIDED PROCEDURES UTILIZING AN IMAGING TOOL AND A POSITION-DETERMINING SYSTEM

CROSS-REFERENCE TO RELATED APPLICATIONS

This application claims priority to German Application No. DE 10 2006 004 793, filed Feb. 2, 2006, the entire content of which are incorporated herein by reference and should be considered a part of this specification.

BACKGROUND OF THE INVENTION

1. Field of the Invention

This invention generally relates to methods and systems for performing coordinate transformation, and in particular, relates to a method and system for performing coordinate transformation for navigation-guided procedures utilizing an imaging tool and a position-determining system.

2. Description of the Related Art

Navigation assistance is increasingly being used in performing medical procedures on living objects. This is typically understood to involve guidance of a medical instrument's movement relative to an area of tissue of the object to be treated. Navigation of the instrument is usually supported by means of a position-determining system. Of special interest is navigation of the instrument in areas that preclude visual monitoring by the surgeon, such as when the instrument is inserted into the interior of the patient. For this purpose, the guidance of the instrument, such as a catheter, is usually performed in a virtual 3D volume generated by means of an imaging method before or during the operation. One common method is to generate a series of 2D projections of a known geometry with the help of an X-ray diagnostic tool and to construct from these 2D images a set of 3D volume data. The set of volume data is transmitted to a navigation system, which provides a position-determining system with markers that can be detected by the system. To realize highly accurate navigation, the coordinate system of the position-determining system is typically aligned with the coordinate system of the 3D set of volume data using a process called "registration." In one example, the registration process uses a phantom, which contains X-ray-positive markers and markers that can be detected by the position-determining system in a fixed spatial relationship relative to each other.

German Patent DE10202091A1 discloses a device and method for determining a coordinate transformation using a phantom, on which X-ray-positive markers and markers that can be detected by a position-determining system are arranged in a fixed spatial relationship relative to each other. During a scan for generating a series of 2D X-ray projections, the coordinates of the X-ray-positive markers are determined in reconstructed 3D volumes and transmitted to the position-determining system and navigation system for alignment.

German OS DE10360025A1 discloses a method of performing coordinate transformation in which markers that can be detected by a position-determining system are arranged on an imaging device, such as an X-ray radiation receiver. One of the disadvantages of this method is that when the image-capturing device is covered by a sterile cover film, the film is interposed between the markers and the position-determining system, which can be disruptive to the position-determining process. In addition, a series of markers in alignment with the device relative to the patient and the position-determining system cannot consistently be detected, which limits the accuracy of a referencing process. Moreover, the X-ray diagnostic tool cannot operate with other types of position-determining system through the markers arranged on the X-ray radiation receiver without mechanical modifications.

German Patent DE19917867B4 discloses a method and device for performing coordinate transformation for an X-ray diagnostic tool wherein a reference structure that can be detected by a position-determining system is connected detachably to the X-ray radiation receiver. After successful registration, the reference structure is removed from the X-ray radiation receiver. One of the disadvantages of this system is that when used in the application of C-arm imaging systems, the distribution of mass in the X-ray diagnostic tool is different in the area of an adjustable C-arm for the registration and diagnostic imaging processes. As such, the kinematics of the X-ray diagnostic tool in terms of the effect of the added mass on the torsion of the C-arm must be taken into account.

Accordingly, one of the objectives of the present invention is to provide an intra-operative procedure and simple and cost-effective means to determine with high accuracy the coordinate transformation between the coordinate system of the position-determining system and the coordinate system of the imaging diagnostic tool, in which the kinematics of the means necessary for image generation are described for navigation-guided procedures using an imaging diagnostic tool that can be adjusted in multiple ways and an arbitrary position-determining system of sufficient accuracy. Here, the terms "image generation" and "imaging" are also understood to include those methods that allow an image to be reconstructed from a series of measured values.

SUMMARY OF THE INVENTION

Certain preferred embodiments of the present invention provide system for performing coordinate transformation for a navigation-guided procedure. The system generally comprises an imaging diagnostic tool that can be adjusted in multiple ways and a position-determining system. The imaging diagnostic tool has at least one spatial reference structure that is arranged on the imaging diagnostic tool. The spatial reference structure can be contacted by a pointer or other contacting tool or device which can be detected by the position-determining system of sufficient accuracy. Preferably, the coordinates of the pointer tip are detected by the position-determining system when the tip makes contact with the reference structure, and the positional information is buffered in a memory. A transformation matrix can be calculated by a computing unit by means of which the coordinate transformation between the coordinate system of the position-determining system and that of the imaging diagnostic tool can be performed recursively. The calculation can be performed from known geometry of the three-dimensional spatial reference structure relative to a coordinate system selected by the manufacturer of the imaging diagnostic tool and stationary relative to this system, and also from the determined coordinates of the contact points. Determining the transformation matrix can be performed according to known computing methods, wherein recursive and iterative methods are applied selectively.

In one embodiment, the invention provides a method for performing coordinate transformation in navigation-guided procedures between an imaging diagnostic tool with at least one reference structure having a known surface geometry and orientation relative to the imaging diagnostic tool, and a position-determining system. The method is characterized in that the reference structure is contacted with the tip of a pointer at three or more contact points, preferably forming a non-isosceles triangle, wherein the tip of the pointer has marks that can be detected by the position-determining system. Preferably, the coordinates of the contacted points are determined by the position-determining system in a coordinate system of the position-determining system and are transmitted to an evaluation computer of the imaging diagnostic tool. Preferably, a transformation matrix is adapted to recursively transform the coordinate systems of the position-determining system and the imaging diagnostic tool one into the other, wherein the transformation matrix is calculated from the coordinates of the contacted points in the coordinate system of the position-determining system, and from the known surface geometry of the reference structure in a coordinate system of the imaging diagnostic tool by a computer program in the evaluation computer.

In another embodiment, the method is characterized in that the reference structure has hemispherical recesses that conforms to the contour of or provide a substantially exact-fit receptacle for at least a portion of the tip of the pointer at the locations of the contact points, and in that when a contact point is touched, the tip of the pointer is pivoted in the corresponding contacted hemispherical recess such that the longitudinal axis of the pointer describes a section of a cone envelop, and that when the pointer is pivoted, the coordinates of the tip of the pointer are detected by the positioning determining system in its coordinate system.

In another embodiment, the method is characterized in that the reference structure has recesses at the locations of the contact points that conform to the contours of or provide a substantially exact-fit receptacle for at least one portion of an anisotropic tip of the pointer in only one orientation, and in that when a contact point is touched, the tip of the pointer is introduced into the corresponding recess with a substantially exact-fit and subsequently the orientation of the tip of the pointer is detected by the position-determining system in its coordinate system.

In another embodiment, the method is characterized in that arbitrary path sections are traversed on the surfaces of the reference structure, preferably fully using the corresponding surface, with the tip of a pointer in contact with the reference structure, and in that during this traversal, the coordinates of the tip of the pointer are detected point-wise by means of the position-determining system in its coordinate system.

In another embodiment, the method is characterized in that from the determining coordinates of the contact points in the coordinate system of the position-determining system and from the known coordinates of the contact points in the coordinate system of the imaging diagnostic tool, a transformation matrix between the two coordinate system is calculated recursively.

In another embodiment, the method is characterized in that with the assistance of an iterative computing method, the reference structure is shifted and pivoted virtually in the coordinate system of the position-determining system and that for each orientation of the reference structure, the sum of the squares of the distances to the contact points to the known surface of the reference structure is determined and the orientation of the reference structure in which the sum of the distances squared is a minimum is used for calculating the transformation matrix.

In another embodiment, the method is characterized in that the coordinates of the tip of the pointer are determined by the position-determining system when the pointer tip is pressed onto the reference structure with a contact force that has a given upper and lower limit, so that the tip of the pointer contacts the reference structure and does not displace the reference structure due to the contact process.

In another embodiment, the method is characterized in that the coordinates of the tip of the pointer are determined by the position-determining system in a time window immediately after the time at which an electrical contact between the tip of the pointer and the reference structure has been detected.

In another embodiment, the method is characterized in that in the presence of a sterile cover film between the tip of the pointer and the reference structure, the coordinates of the tip of the pointer are determined by the position-determining system after visual inspection of the sterile cover film for creases in the area of the contact point, and the thickness of the film is taken into account in the determination of the transformation matrix.

In another embodiment, the method is characterized in that the imaging diagnostic tool assumes an orientation that is substantially insensitive to the effect of mechanical forces during the tracing of the reference structure, and the adjustment axes of the imaging diagnostic tool are locked.

In another embodiment, the method is characterized in that the pointer is oriented by the operator during the contact at a contact point such that substantially all of the markers of the pointer are detected by the position-determining system.

In another embodiment, the method is characterized in that the coordinate transformation maintains its validity until the controller of the imaging diagnostic tool detects that the imaging diagnostic tool has been adjusted beyond the pre-designed adjustment area.

In another embodiment, the present invention provides a device for performing any of the above-described functions. The device is characterized in that the reference structure has at least three contact points which can be touched by a pointer having markers that can be detected by a position-determining system, and a non-isosceles triangle is formed by the three points, and wherein the contact points are arranged on the image-capture unit of the imaging diagnostic tool.

In another embodiment, the device is characterized in that the reference structure has at least three contact points which can be contacted by a pointer having markers that can be detected by a position-determining system, wherein a non-isosceles triangle is formed by the three points, and wherein the contact points are arranged on a carrier structure of the imaging diagnostic tool. Preferably, the imaging diagnostic tool is selected from the group consisting of computer tomography, x-ray diagnostic tool, nuclear magnetic resonance tomography, and ultrasound imaging tool. Preferably, the carrier structure comprises a horizontal guide, and wherein the imaging diagnostic tool is a mobile X-ray diagnostic tool equipped selectively for 2D or 3D navigation.

In another embodiment, the device is characterized in that the reference structure comprises a body with a known anisotropic surface geometry, wherein the surface can be touched by a pointer device and has at least three contact points, wherein the three contact points form a non-isosceles triangle, wherein the contact points are arranged on the image-capture unit of the imaging diagnostic tool.

In another embodiment, the preferred embodiments of the present invention provide a system for performing coordinate transformation for navigation-guided procedures. The system comprises a mobile imaging system, a position-determining system, a three-dimensional reference structure disposed on the mobile imaging system, wherein the three-dimensional reference structure comprises an asymmetrical contact surface. The system further comprises a pointer adapted for contacting a plurality of locations on the asymmetrical contact surface, wherein the pointer comprises a plurality of markers, wherein the position of the markers is detected by the position-determining system.

DETAILED DESCRIPTION OF THE PREFERRED EMBODIMENT

Figure 1:
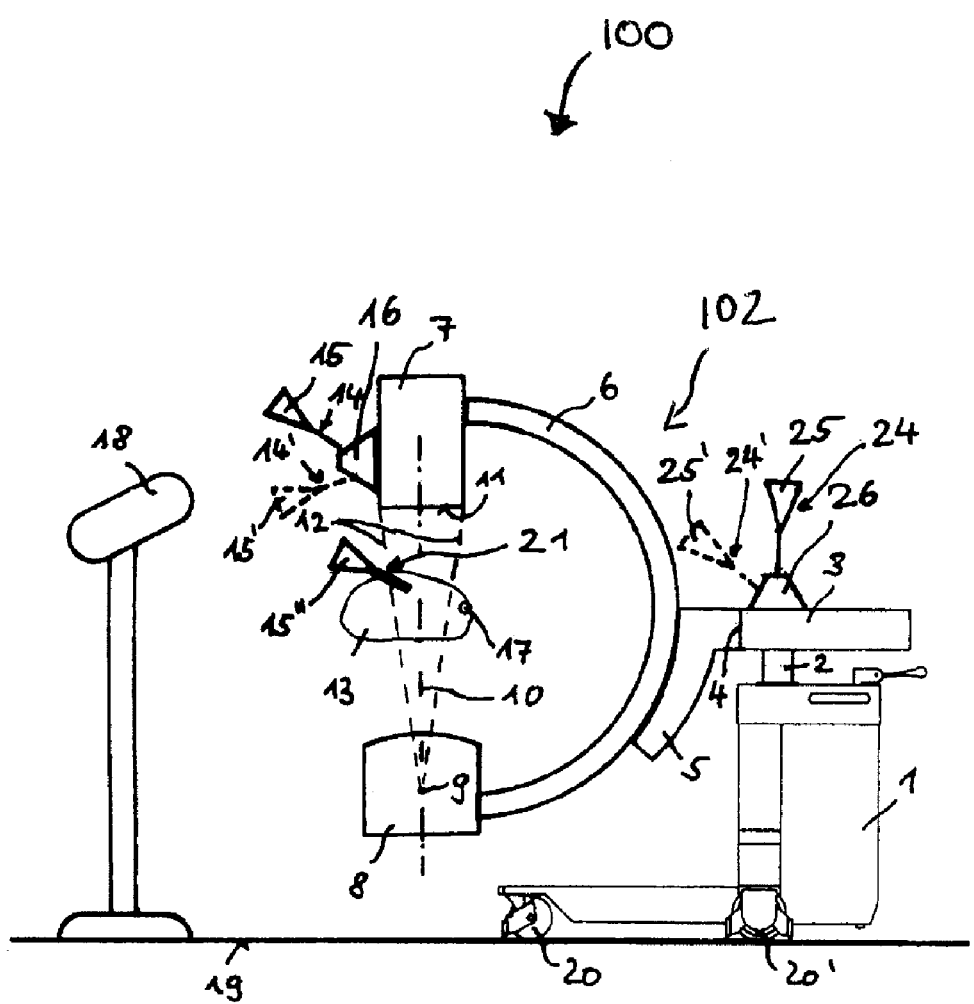
FIG. 1 illustrates a system of one preferred embodiment of the present invention.

FIG. 1 schematically illustrates a system 100 of one preferred embodiment of the present invention configured for performing coordinate transformation for navigation-guided medical procedures utilizing an imaging diagnostic tool and a position-determining system. As will be described in greater detail below, the system generally includes a medical imaging device incorporating one or more reference structures that work in conjunction with a position-determining system.

In FIG. 1, the system 100 generally includes a medical imaging device 102 having a plurality of reference structures 16, 26 attached thereto, and a position-determining system 18. The medical imaging device 102 is shown in the form of a mobile X-ray diagnostic machine with a device cart 1 that can move on rollers 20, 20' along the floor 19. The medical imaging device 102 further includes a C-arm 6 that is connected to the device cart 1 and can be adjusted in multiple ways. In one embodiment, the medical imaging device include an X-ray radiation source 8 and an X-ray radiation receiver 7, which are arranged at the ends of the C-arm 6 that is mounted in a C-arm holder 5 so that it can move along its periphery about the center 17. Preferably, the C-arm holder 5 is mounted on the device cart 1 so that it can be adjusted in multiple ways. In one implementation, the C-arm holder 5 is mounted with a pivot bearing 4 on a horizontal guide 3 so that it can pivot about a horizontal axis. The horizontal guide 3 is mounted on the column 2 so that it is adjustable in height and can rotate about the vertical axis of the column 2. Preferably, all or at least some of the adjustable components of the C-arm 6 are equipped with position-measuring sensors whose measurement values are fed to a central motion controller of the X-ray diagnostic machine. Preferably, all or at least some of the adjustment axes are configured so that they can be selectively locked in position, individually or all together, by brakes. In one embodiment, the rollers 20, 20' are equipped with an immobilization brake. Preferably, the adjustment motion of the C-arm in the holder (orbital motion), the adjustment in the horizontal guide 3, and the vertical adjustment in the column are performed by electric motor. Preferably, the motors arranged in the adjustment axes are controlled by a central motion controller for the X-ray diagnostic machine. In one embodiment, a decisive condition is that the positions of all of the adjustment axes that need to be adjusted for obtaining diagnostic images or image data sets during an examination are each detected through suitable position sensors, and that the adjustment axes that have no position sensors are locked in a reproducible way in a fixed position during the examination. Under such conditions, the kinematics of the X-ray radiation source 8 and the X-ray radiation receiver 7 are predictable as a function of the ordered series of the measurement values of the position sensors. For this purpose, the kinematics of the X-ray diagnostic tool are typically measured with suitable means before delivery to the customer in order to take into account the torsion of the C-arm, which is specific to each device but is reproducible. In practice, the deviations between the observed kinematics and the kinematics of a non-twisted, circular arc-shaped C-arm are stored in look-up tables in the controller or image-processing computer of the X-ray diagnostic tool, and referenced for the reconstruction of the X-ray projection geometry.

FIG. 1 also schematically shows a reference structure 16 that in one embodiment is arranged on the X-ray radiation receiver 7. In the embodiment shown in FIG. 1, the reference structure 16 comprises a truncated pyramid. Points or surfaces of the reference structure 16 are configured to be contacted by means of a pointer 14, 14'. The position of the tip of the pointer 14, 14' can be determined via detection of the position in space of the marker arrangement 15, 15' attached to the pointer 14 by the position-determining system. Preferably, the knowledge of the geometry of the pointer 14, assumed to be a rigid body, is included in the calculation of the position.

The pointer 14, 14' can be made to contact the reference structure 16 by an operator through point contact, wherein suitable measures ensure that the X-ray radiation receiver 7 and the C-arm 6 are not elastically or permanently displaced by too strong of a contact pressure of the pointer on the reference structure. These measures can include providing a force limiter in the reference structure 16 or in the pointer 14, 14', for example. It is further provided to move the device for generating images in the medical imaging device into a set parked position before contacting the reference structure 16 with the pointer 14. In this parked position, the device for image capture via contact with the pointer 14 is substantially insensitive to the contact force. In the example of the X-ray diagnostic machine shown in FIG. 1 with the reference structure 16 arranged on the X-ray radiation receiver 7, the setting in the parked position is preferably selected in which the X-ray radiation receiver 7 is situated in the direct vicinity of the horizontal guide 3 at the end of the adjustment range of the C-arm holder 5.

Furthermore, FIG. 1 shows another reference structure 26, which in the embodiment illustrated, is arranged on the horizontal guide 3 and can be contacted or touched with a pointer 24, 24' having a marker arrangement 25, 25' attached thereto. The imaging diagnostic machine can be selectively equipped with just one of the two reference structures 16, 26; however, in the scope of the invention two reference structures 16, 26, and if necessary additional, not-shown reference structures can be provided. Preferably, the individual reference structures differ in their three-dimensional construction such that they can be readily and automatically identified by the contact process.

Figures 2A, 2B:
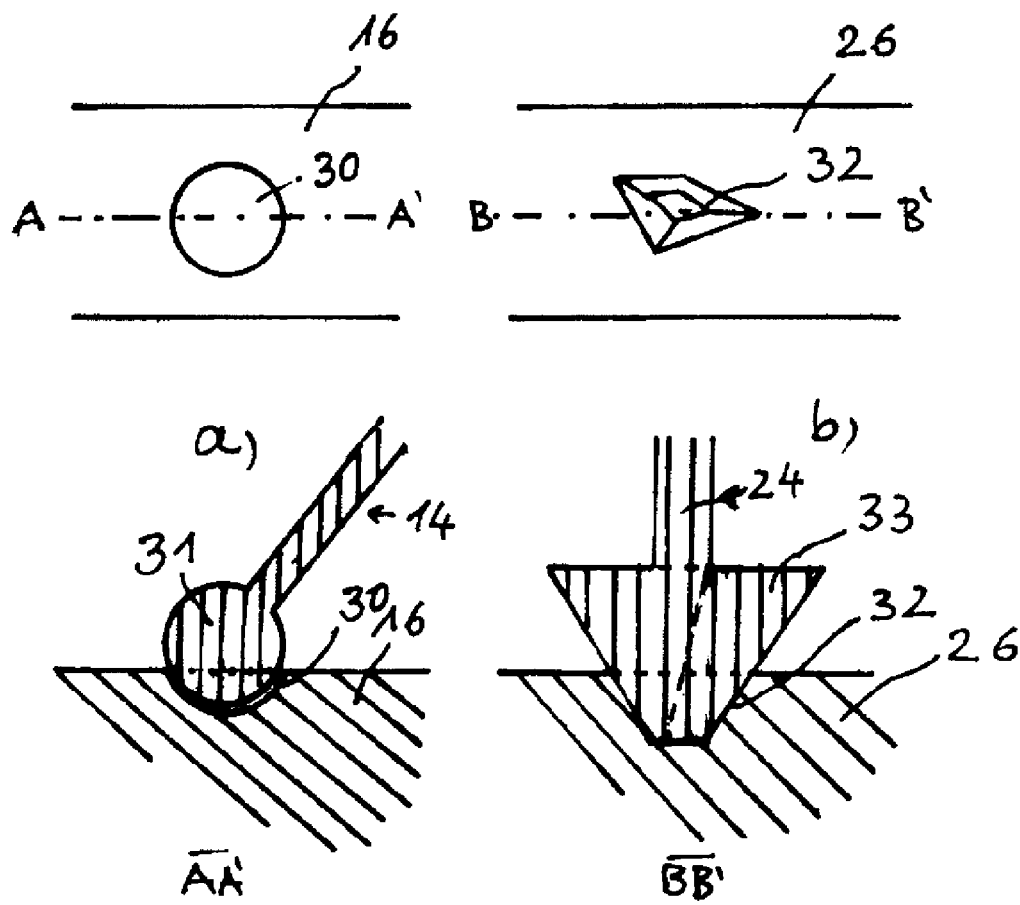
FIGS. 2A and 2B illustrate top view and cross-sectional view of reference structures of certain preferred embodiments.

FIGS. 2A and 2B illustrate details of the reference structures 16, 26 according to certain preferred embodiments of the invention. FIG. 2A shows a top view and a cross-sectional view of the reference structure 16. As shown in FIG. 2A, the reference structure 16 has a hemispherical recess 30 formed on its surface. This recess 30 provides a substantially exact-fit receptacle for at least a portion of a spherical tip 31 of a pointer 14. Preferably, at least a portion of the contour of the spherical tip 31 corresponds to the inscribed bowl defined by the recess 30. A hemispherical recess 31 can also be used in the sterile area of an imaging diagnostic machine as a contact point for a spherical tip 31 of a pointer 14. A 20-30 μm thick sterile cover film can also be enclosed between the spherical tip 31 and the hemispherical recess 30. The thickness of the film can be taken into account in the coordinate transformation. In practice, the pointer 14 with the spherical tip 31 is introduced by an operator into the hemispherical recess 30 as shown in FIG. 2A and moved in a manner such that the longitudinal axis of the pointer 14 describes a cone-envelope surface or a section of this surface. The position-determining system 18 in turn determines the position of the center of the spherical tip 31 several times during the motion of the pointer, then uses the knowledge that the spherical tip 31 is typically always located at the same position in space, the position of the spherical tip 31 can be determined with significantly higher accuracy than would be possible with a single measurement.

FIG. 2B shows the reference structure having a truncated pyramid-shaped recess 32 in a reference structure 26, in top view and in cross-sectional view. At least a portion of a truncated pyramid tip 33 on a pointer 24 fitting substantially exactly into this truncated pyramid-shaped recess 32 is detachably arranged in the recess 32. Certain preferred embodiments of the invention provide for the truncated pyramid tip 33 to be held on the reference structure 26 not by hand, but rather by spring force, magnetic force, or by a not-shown mechanical latching device during the position determination by the position-determining system 18. In one embodiment, the imaging diagnostic machine can have several truncated pyramid-shaped recesses 32 into which the truncated pyramid tip 33 of the pointer 24 can be used to contact one after the other. In the example shown in FIG. 2B, a truncated pyramid tip 32 is shown as the pointer tip. In the scope of the invention, however, the shape of the tip can be changed within broad limits. In a preferred embodiment, a unique orientation of the pointer is provided. For example, the tip of the pointer preferably does not exhibit any symmetry relative to the pointer axis. Due to a preferably polygonal shape, or a shape with small curvature radii, of the recess, it is often not possible in practice to provide such a recess in the sterile area as a sterile cover film either would be punctured when the truncated pyramid tip 32 is pushed into the truncated pyramid-shaped recess 31 and therefore made unusable, or the tip could not be pushed into the recess—for example, due to a wrinkling of the film. Therefore, such a reference structure is preferably not provided in the non-sterile area of the imaging diagnostic tool, for example, on the surface of the horizontal guide 3.

Figure 3:
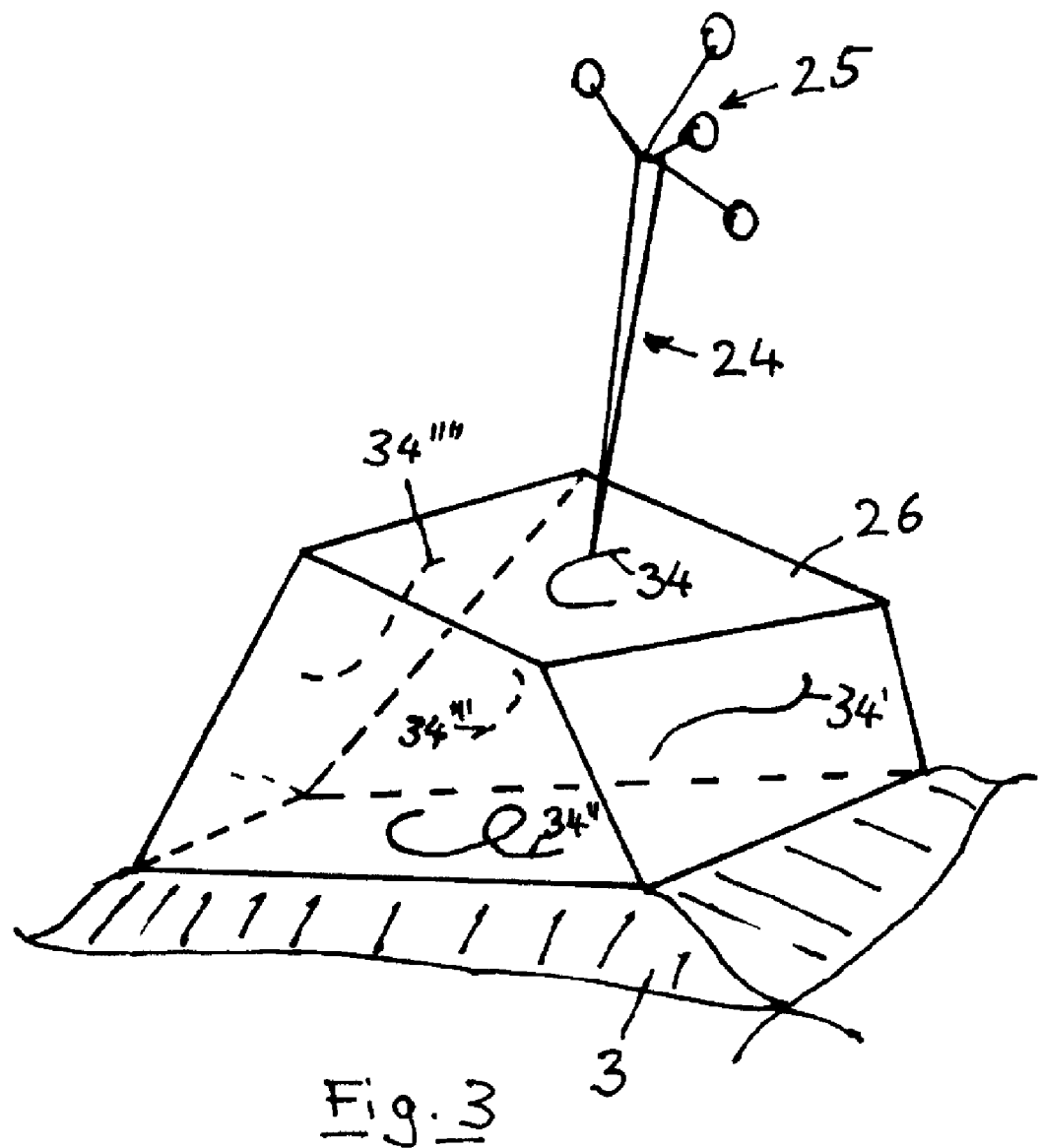
FIG. 3 illustrates path sections of a pointer tip on a reference structure of a preferred embodiment.

FIG. 3 shows one embodiment of the path of pointer 24 tip formed from path sections 34, 34', 34", 34''', 34'''' with a marker arrangement 25 connected to the pointer 24. The path sections 34, . . . 34'''' are realized in that the pointer 24 is successively moved by an operator, with its tip in contact with a reference structure, on the surfaces of this reference structure 26 shown in the example of FIG. 3 as an oblique truncated pyramid. The position-determining system 18 detects the motion of the tip of the pointer 24 in space at a given measurement clock rate and transmits the position vectors of the path sections 34, . . . 34'''' in a suitable format, for example, as a series of points or as vector graphics, to an evaluation computer of the diagnostic tool where the sum of the experimentally determined path sections 34, . . . 34'''' is adapted to the known surface geometry of the reference structure 26 by a "best fit" method. In this way, the position of the reference structure 26 is determined very precisely in terms of the coordinate system of the position-determining system 18, whereby the accuracy of the coordinate transformation can be determined with high accuracy due to the nature of the system of equations. For example, if a single point on the reference structure 26 is traversed and touched with the pointer 24, then the position of the contact point can be calculated from the position of the markers 25 through addition of a vector that is unique to the pointer 24. If the pointer tip persists on the single contact point and if the shaft of the pointer 24 with the markers 25 is pivoted in space, then the position of the contact point can be determined with higher accuracy than would be possible for a single touch by means of the least squares method.

During the contact processes, it preferably should be ensured that the imaging diagnostic device is not elastically deformed or permanently displaced by the contact force. In one embodiment, the contact force is monitored, for example, by means of a piezoelectric sensor in the pointer tip. For this reason, touch processes, for example, with impermissibly high contact forces can be excluded from the calculation of the coordinate transformation. Furthermore, the contact time of the pointer tip on the reference structure is determined electromagnetically or visually for point-wise contact. For example, the position-determining system 18 would determine the coordinates of the marker arrangement integrated into the pointer only at the time of contact.

In the example of the path sections 34, . . . 34'''' on the truncated pyramid surfaces, these are adapted to the truncated pyramid-shaped reference structure 26 according to known mathematical methods of error calculation. To be able to perform a coordinate transformation using a truncated pyramid-shaped reference structure 26, the truncated pyramid is preferably shaped so that when it is rotated about an arbitrary axis it returns to the same position after rotation by at most 360 degrees. This condition is satisfied, for example, by an oblique truncated pyramid, as shown schematically in FIG. 3.

For the case in which the coordinate transformation is to be calculated from determining the positions of individual contact points, at least four measurement points not lying in the same plane on the reference structure 26 are to be contacted. Alternatively, three measurement points, which define a plane and which preferably do not form an isosceles triangle, could also be contacted, and the determination of the coordinate system of the diagnostic tool could be calculated by applying a convention to be established. For example, if one selects three measurement points on the reference structure 26 such that they form a non-isosceles, right triangle, then a convention might be, for example: the vertex of the triangle with the right angle is selected as the coordinate origin, the longer leg of the triangle—viewed from the coordinate origin—gives the direction of the x-axis, the shorter leg of the triangle—viewed from the coordinate origin—gives the direction of the y-axis, and the z-axis points in the direction of the vector product of the vector of the x-axis and the vector of the y-axis. The condition that the three measurement points span a right triangle is not absolutely necessary. Thus, for example, the vertex subtended by the longest side and the second longest side of the triangle can be defined as the coordinate origin, the longest side can be defined as the x-axis, and the z-axis can be defined in the direction of the vector product of the side vectors of the longest and the second longest side. The y-axis lies in the plane spanned by the three points of the triangle and is perpendicular to the x-axis.

The position-determining system 18 can be an optical system (infrared system), electromagnetic system, or a system based on the measurement of a magnetic field or the gravitational field of the earth.

Navigation can be provided for an instrument 21 detected by the position-determining system 18 in FIG. 1 with markers 15'', for example, in a reconstructed 2D or 3D X-ray model, a CT volume, an ultrasound volume, or a magnetic resonance volume, after the registration procedure. That is, the movements of the instrument 21 can be tracked by a surgeon on a monitor with reference to a schematically displayed model of the instrument 21 in a reconstructed 2D or 3D model of the real patient space. This is especially advantageous when the work area of the instrument 21, for example, the tip of a drill, is not perceptible to the surgeon in the visible range of the electromagnetic spectrum.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. A method for performing coordinate transformation in navigation-guided procedures between an imaging diagnostic tool with at least one reference structure having a known surface geometry and orientation relative to the imaging diagnostic tool, and a position-determining system, comprising:
    positioning the at least one reference structure adjacent to the imaging diagnostic tool, said at least one reference structure comprising a plurality of truncated pyramid-shaped recesses;
    tracing the at least one reference structure by contacting the at least one reference structure with the tip of a pointer at three or more contact points forming a non-isosceles triangle, wherein the tip of the pointer has markers that can be detected by the position-determining system,
    determining the coordinates of the contacted points by the position-determining system in a coordinate system of this position-determining system and are transmitted to an evaluation computer of the imaging diagnostic tool,
    wherein the imaging diagnostic tool assumes an orientation that is substantially insensitive to the effect of mechanical forces during the tracing of the reference structure, and adjustment axes of the imaging diagnostic tool are locked such that the kinematics of the imaging diagnostic tool are predicted as a function of the ordered series of measurement values of position sensors located on the imaging diagnostic tool, and
    recursively transforming the coordinate systems of the position-determining system and the imaging diagnostic tool one into the other with a transformation matrix, wherein the transformation matrix is calculated from the coordinates of the contacted points in the coordinate system of the position-determining system, and from the known surface geometry of the reference structure in a coordinate system of the imaging diagnostic tool, by a computer program in the evaluation computer.

2. The method according to claim 1, wherein the reference structure has hemispherical recesses that provide a receptacle that substantially conforms to the contour of at least a portion of the tip of the pointer at the locations of the contact points, and in that when a contact point is touched, the tip of the pointer is pivoted in the corresponding contacted hemispherical recess such that the longitudinal axis of the pointer describes a section of a cone envelope, and in that when the pointer is pivoted the coordinates of the tip of the ball of the pointer are detected by the position-determining system in its coordinate system.

3. The method according to claim 1, wherein the reference structure has recesses at the locations of the contact points that provide a receptacle that substantially conforms to the contours of at least a portion an anisotropic tip of the pointer only in one unambiguous orientation, and in that when a contact point is touched, the tip of the pointer is introduced into the corresponding recess with a substantially exact fit and subsequently the orientation of the tip of the pointer is detected by means of the position-determining system in its coordinate system.

4. The method according to claim 3, wherein calculating the transformation matrix from the coordinates of the contacted points in the coordinate system of the position-determining system, and from the known surface geometry of the reference structure comprising using a reference structure has anisotropic recesses at the locations of the contact points that provide a substantially exact-fit and detachable receptacle for the tip of the pointer in an unambiguous orientation.

5. The method according to claim 1,
    wherein arbitrary path sections are traversed on the surfaces of the reference structure with the tip of a pointer in contact with the reference structure, and in that during this traversal the coordinates of the tip of the pointer are detected point-wise by means of the position-determining system in its coordinate system.

6. The method according to claim 5,
    wherein with the assistance of an iterative computing method, the reference structure is shifted and pivoted virtually in the coordinate system of the position-determining system and that for each orientation of the reference structure the sum of the squares of the distances to the contact points to the known surface of the reference structure is determined and the orientation of the reference structure in which the sum of the distances squared is a minimum is used for calculating the transformation matrix.

7. The method according to claim 1,
    wherein from the determined coordinates of the contact points in the coordinate system of the position-determining system and from the known coordinates of the contact points in the coordinate system of the imaging diagnostic tool, a transformation matrix between the two coordinate systems is calculated recursively.

8. The method according to claim 1,
    wherein the coordinates of the tip of the pointer are determined by the position-determining system when the pointer tip is pressed onto the reference structure with a contact force that has a given upper and lower limit, so that it is ensured that the tip of the pointer contacts the reference structure and does not displace the reference structure due to the contact process.

9. The method according to claim 1,
    wherein the coordinates of the tip of the pointer are determined by the position-determining system in a time window immediately after the time at which an electrical contact between the tip of the pointer and the reference structure has been detected.

10. The method according to claim 1,
    wherein in the presence of a sterile cover film between the tip of the pointer and the reference structure, the coordinates of the tip of the pointer are determined by the position-determining system after visual inspection of the sterile cover film for presence of creases in the area of the contact point, and the thickness of the film is taken into account in the determination of the transformation matrix.

11. The method according to claim 1,
    wherein the pointer is oriented by the operator during the contact at a contact point such that substantially all of the markers of the pointer are detected by the position-determining system.

12. The method according to claim 1,
wherein the coordinate transformation maintains its validity until the controller of the imaging diagnostic tool detects that the imaging diagnostic tool has been adjusted beyond the designed adjustment area.

13. The method according to claim 1, wherein contacting the at least one reference structure with the tip of a pointer at three or more contact points forming a non-isosceles triangle comprises arranging the contact points on an image-capture unit of the imaging diagnostic tool.

14. The method according to claim 1, wherein contacting the at least one reference structure with the tip of a pointer at three or more contact points forming a non-isosceles triangle comprises arranging the contact points on a carrier structure of the imaging diagnostic tool.

15. The method according to claim 14,
wherein the carrier structure comprises a horizontal guide, wherein the imaging diagnostic tool comprises a mobile X-ray diagnostic tool equipped selectively for 2D or 3D navigation.

16. The method according to claim 1, further comprising selecting the imaging diagnostic tool from the group consisting of computer tomography, an X-ray diagnostic tool, nuclear magnetic resonance tomography, and an ultrasound imaging tool.

17. The method according to claim 1, wherein calculating the transformation matrix from the coordinates of the contacted points in the coordinate system of the position-determining system, and from the known surface geometry of the reference structure comprising using a reference structure comprises a body with a known, anisotropic surface geometry, and wherein the contact points are arranged on the image-capture unit of the imaging diagnostic tool.

\* \* \* \* \*